(12) United States Patent
Von Herzen et al.

(10) Patent No.: US 9,389,215 B2
(45) Date of Patent: Jul. 12, 2016

(54) MULTI-MODAL FLUID CONDITION SENSOR PLATFORM AND SYSTEM THEREOF

(71) Applicant: MASTINC, New York, NY (US)

(72) Inventors: Brian Von Herzen, Minden, NV (US); Steven Van Fleet, Lagrangeville, NY (US); Hamish Fallside, Monte Sereno, CA (US); Randall Hall, Santa Cruz, CA (US)

(73) Assignee: MASTINC, New York, NY (US)

( * ) Notice: Subject to any disclaimer, the term of this patent is extended or adjusted under 35 U.S.C. 154(b) by 166 days.

(21) Appl. No.: 13/844,139

(22) Filed: Mar. 15, 2013

(65) Prior Publication Data

US 2014/0130587 A1    May 15, 2014

Related U.S. Application Data

(63) Continuation-in-part of application No. 13/731,659, filed on Dec. 31, 2012, now Pat. No. 8,924,166, which is a continuation of application No. 13/621,599, filed on Sep. 17, 2012.

(60) Provisional application No. 61/538,282, filed on Sep. 23, 2011.

(51) Int. Cl.
*G01N 33/28* (2006.01)
*G01N 27/02* (2006.01)
(Continued)

(52) U.S. Cl.
CPC ............ *G01N 33/2888* (2013.01); *F01M 11/10* (2013.01); *F16N 2250/00* (2013.01); *F16N 2270/50* (2013.01); *G01M 15/042* (2013.01); *G01N 27/02* (2013.01)

(58) Field of Classification Search
CPC .... G01M 15/042; G01M 15/05; F01M 11/10; F16N 2250/00; F16N 2270/50; G01N 33/2888; G01N 27/02
USPC ............ 702/50, 86; 210/85; 73/61.59, 53.05; 192/101, 103 C
See application file for complete search history.

(56) References Cited

U.S. PATENT DOCUMENTS 5,105,372 A * 4/1992 Provost et al. ................ 702/185
5,884,601 A    3/1999 Robinson
(Continued)

FOREIGN PATENT DOCUMENTS

DE    10 2004 032 538        1/2006
DE    102004032538 A1 *      1/2006
(Continued)

OTHER PUBLICATIONS

International Search Report issued in co-pending International Application No. PCT/US2014/025606 mailed Sep. 9, 2014.
(Continued)

*Primary Examiner* — Carol S Tsai
(74) *Attorney, Agent, or Firm* — Fanelli Haag PLLC

(57) ABSTRACT

This invention encompasses embodiments for multi-modal integrated simultaneous measurement of various aspects of fluids contained in circulating systems such as automotive reciprocating engines and vehicle transmissions. These circulating systems perform constant internal lubrication, and heat and contaminant removal to protect the internal moving parts from the inherent friction and damage in normal operation. Most commonly this is achieved with fluids based on hydrocarbon and/or related synthetics, which, over time, can lose their protective properties, and vary in their performance or breakdown/decay due to internal and external events. Several components within the lubricant fluid can be measured and can provide insight into the efficacy of the system to perform its designed mission. The mass and level of the fluid may also be monitored on an on-going basis. Described herein is a real-time, simultaneous, integrated, multi-modal sensor system for early warning notification.

34 Claims, 7 Drawing Sheets

(51) Int. Cl.
*F01M 11/10* (2006.01)
*G01M 15/04* (2006.01)

(56) References Cited

U.S. PATENT DOCUMENTS

| | | | |
|---|---|---|---|
| 6,157,894 A | 12/2000 | Hess et al. | |
| 6,298,834 B1 * | 10/2001 | Thead et al. | 123/549 |
| 6,324,899 B1 | 12/2001 | Discenzo | |
| 6,546,785 B1 | 4/2003 | Discenzo | |
| 6,860,142 B2 | 3/2005 | Seevers et al. | |
| 6,868,325 B2 * | 3/2005 | Menon et al. | 701/100 |
| 6,877,360 B1 | 4/2005 | Discenzo | |
| 6,928,965 B2 | 8/2005 | Teufl | |
| 6,957,586 B2 | 10/2005 | Sprague | |
| 7,134,323 B1 | 11/2006 | Discenzo | |
| 7,442,291 B1 * | 10/2008 | Discenzo et al. | 210/85 |
| 7,649,806 B2 | 1/2010 | Didier | |
| 7,695,300 B2 * | 4/2010 | Leccia et al. | 439/263 |
| 8,159,549 B2 * | 4/2012 | Glukhovsky | A61B 1/00009 348/22 |
| 8,464,684 B2 | 6/2013 | Kusel | |
| 8,643,388 B2 * | 2/2014 | Hedges | 324/698 |
| 8,700,114 B2 | 4/2014 | Gottlieb et al. | |
| 8,764,672 B2 | 7/2014 | Manwaring et al. | |
| 8,820,147 B2 | 9/2014 | Sinha | |
| 2003/0102050 A1 * | 6/2003 | Matthews | F01M 11/04 141/65 |
| 2005/0066711 A1 | 3/2005 | Discenzo | |
| 2010/0109331 A1 | 5/2010 | Hedtke et al. | |
| 2010/0294231 A1 | 11/2010 | Kusel | |
| 2011/0169512 A1 | 7/2011 | Hedges | |
| 2012/0025529 A1 | 2/2012 | Davis et al. | |
| 2012/0186445 A1 * | 7/2012 | Geissler | F01B 31/12 92/5 R |
| 2013/0030643 A1 | 1/2013 | Nishizawa | |
| 2013/0080085 A1 | 3/2013 | Von Herzen et al. | |

FOREIGN PATENT DOCUMENTS

| | | |
|---|---|---|
| WO | WO 2009/106711 | 9/2009 |
| WO | WO 2009106711 A2 * | 9/2009 |
| WO | WO 2010/133272 | 11/2010 |

OTHER PUBLICATIONS

Final Office Action issued in co-pending U.S. Appl. No. 13/731,659 mailed Mar. 4, 2014.
Final Office Action issued in co-pending U.S. Appl. No. 13/621,599 mailed Mar. 6, 2014.
Non-Final Office Action issued in co-pending U.S. Appl. No. 13/621,599 mailed Jul. 7, 2014.
Non-Final Office Action issued in co-pending U.S. Appl. No. 13/731,659 mailed Jun. 30, 2014.
Non-Final Office Action issued in co-pending U.S. Appl. No. 13/731,647 mailed Oct. 9, 2014.
Notice of Allowance issued in co-pending U.S. Appl. No. 13/621,599 mailed Oct. 15, 2014.
Final Office Action issued in co-pending U.S. Appl. No. 13/731,647 mailed Apr. 17, 2015.
Non-Final Office Action issued in U.S. Appl. No. 14/523,526, mailed Sep. 18, 2015.
Non-Final Office Action issued in U.S. Appl. No. 14/554,414, mailed Sep. 18, 2015.
Non-Final Office Action issued in co-pending U.S. Appl. No. 13/840,452 mailed Feb. 12, 2015.

* cited by examiner

MULTI-MODAL FLUID CONDITION SENSOR PLATFORM AND SYSTEM THEREOF

FIELD OF THE INVENTION

This invention encompasses embodiments for multi-modal integrated simultaneous measurement of various aspects of fluids contained in circulating systems such as automotive reciprocating engines and vehicle transmissions. These circulating systems perform constant internal lubrication, and heat and contaminant removal to protect the internal moving parts from the inherent friction and damage in normal operation. Most commonly this is achieved with fluids based on hydrocarbon and/or related synthetics, which, over time, can lose their protective properties, and vary in their performance or breakdown/decay due to internal and external events. Several components within the lubricant fluid can be measured and can provide insight into the efficacy of the system to perform its designed mission. Described herein is a real-time, simultaneous, integrated, multi-modal sensor system for early warning notification.

BACKGROUND OF THE INVENTION

This field of invention is related, but not limited to, the automobile industry. In particular, the field relates to mechanical engines and large-scale mechanical devices that utilize motile lubricating fluids operating in high temperature environments. For these lubricants, it would be beneficial to monitor in real-time the changing fluid properties, the levels of contaminants, and changes in performance to ensure safe and reliable operation of the equipment being protected by the lubricating system. This approach applies to automotive vehicles, aircraft or spacecraft, industrial equipment, wind-turbines, life-saving medical machinery and other critical devices. The conditions of fluids are often detected using a static, periodic approach, typically requiring removing fluid from the system, often by extracting a sample of the fluid to send to testing laboratories around the world, which have established procedures and methods to measure a number of aspects of the lubricating fluid, including historical time-series of various parameters. It is common practice to apply such time-based longitudinal monitoring of the fluid to detect changes over time to gain an understanding of the changes in performance within the closed environment. For example, the presence of specific particles at increasing concentrations can indicate levels of wear and performance of certain underlying components within the system being lubricated. This testing typically measures changes in characteristics of the fluid over time, including detecting changes and deterioration of underlying lubricating fluid and additives and the detection of normal (expected) and abnormal (unexpected) "wear" of the moving parts due to normal operation. Static samples are usually sent to a facility that performs a number of tests, including detecting the presence of foreign materials and objects. In some cases, such as when the lubrication fluid is changed, the lubrication filter is commonly sent as well as the oil for testing and detailed analysis. For both the sample and the filter, this is a destructive "tear down" analysis—such that the filter and the sample are not returned to service, but evaluated and subsequently removed. Tests typically performed in the laboratory include detection of metallic and non-metallic particles, presence of water or other non-lubricant liquids, carbon soot and other components, and in some cases, verification that the underlying chemistry of the lubricant is still intact. A written (or electronic) report is generated and transmitted to the stakeholder upon completion of the testing. Results typically take days or weeks from extraction to stakeholder review.

A number of low-cost lubricating fluid measurement products and techniques are emerging onto the market—including a consumer static "check" of a motor oil sample (see lubricheck.com) which measures the changes in electrical impedance characteristics (electrical capacitance and resistance when a small electrical source is applied across the sensor where a sufficient sample size of the lubricant bridges the sensor electrode across to the detector). This approach performs a single-dimensional measurement of oil sump fluid properties at a point in time in the evolution of the oil (i.e. a static measurement), providing insight only when the operator manually extracts a sample of oil to be tested and only indicates changes in the electrical properties should the data be appropriately logged and tracked over time. This approach has many drawbacks including the interval sampling (only when the operator makes a measurement), as well as the potential for counteracting forces from the presence of multiple contaminants introduced into the fluid to mask the true state/condition of the lubricant. As an example, in the case of an automobile engine, the normal operation of the combustion engine will produce carbon by-products as a result of the operation of the engine (this is what discolors the oil). If a vehicle were producing only this carbon "soot" the resistance would change (increase) due to the introduction of the soot. If at the same time, the engine were undergoing adverse 'wear' to the extent that small metallic particles were produced as an abnormal condition across the internal moving parts, these particles would decrease the resistance, as metal is a better conductor over the base lubricant. In the case where both soot and metallic particles were being produced at the same time, they could partially or completely cancel out some or all the measurable effects—thus providing a false indication of the true condition of the lubricant and underlying engine. A testing laboratory analysis by comparison performs a number of tests which would be able to independently detect the presence of both materials in the base lubricant fluid and provide an accurate report of the condition of the fluid and the resulting system.

Lubricating fluids have to accommodate a wide range of operating conditions—including variances in temperature, pressure, purity, and state change. Lubricants are often optimized for a specific operating environment and temperature range and are expressed in viscosity. Some lubricants are designed to operate with multiple viscosities (e.g., 10W-30 multi-grade viscosity motor oil). Typically, measurement of the fluid condition and properties is static and performed externally outside this operating environment via sampling when in a static/non-operating state. Static sampling does not necessarily validate the condition of the fluid in the operating state—either within or outside the normal/typical operating range. There are expensive and complex sensors that have been developed for measuring lubricating fluid and other liquids in real time—either for use in laboratory environments and conditions or for very high-value machinery where immediate sensor lubrication information is critical. Companies such as Voelker Sensors, Inc. offer a product for the machine tool industry that measures in real time a number of parameters including oil level, oxidation (change in pH), temperature, etc. The sensor element is not MEMS based and has a larger footprint, and is not suitable in size/form factor for operation within automobile oil/lubrication systems ("*Continuous Oil Condition Monitoring for machine Tool and Industrial Processing Equipment,*" *Practicing Oil Analysis* (9/2003).

Outside of the field of integrated-circuit multimodal sensor systems, there have been various implementations of continuous electrical property measurements as performed by Halalay (U.S. Pat. Nos. 7,835,875, 6,922,064, 7,362,110), Freese et al., (U.S. Pat. No. 5,604,441), Ismail et al., (U.S. Pat. No. 6,557,396), Steininger (U.S. Pat. No. 4,224,154), Marszalek (U.S. Pat. No. 6,268,737), and others which disclose either a singular vector analysis (electrical) or a time series measurement of electrical properties to derive an understanding of the oil condition. The challenge remains, as in the Lubricheck approach, to overcome the interdependent and true measurement cancelling effects that can report an incorrect oil condition. This is precisely why the fluid testing protocols and laboratories apply tests across multiple dimensions to include spectral analysis as well as tests to determine metal and other foreign object content in the oil samples.

Lubricants are designed to perform beyond their stated range and are further enhanced through the addition of "additives" to extend the lifetime and safety margin of the fluid. Understanding the lubrication longevity is crucial for the safe operation of the system. Replacement of the fluid is performed typically at very conservative (i.e. short) recommended intervals, providing a wide safety margin for the operator. In general, lubricants can operate for significantly longer intervals, or in the case of specific equipment operating in harsh environments (e.g. military equipment used on the battlefield or in mining operations, etc.) may require a more aggressive replacement cycle. It is important to determine when the lubricating fluid cannot continue to perform according to specifications determined by the equipment/system manufacturers. As long as the lubricating fluid is within the safe margin of operation, it may operate indefinitely and not need to be exchanged or replaced with fresh lubricating fluid.

Providing a more precise measure of the fluid's performance can maximize the lifetime of both the lubricant and the equipment the lubricant is protecting. As the cost of the equipment and the hydrocarbon lubricant increase, so does the value of providing both a longer and more precise lifetime of the lubricant and early detection and notification of pending equipment performance deterioration (including motor, filter, and other components in the system, etc.). This approach can potentially save lives when critical equipment failures are detected in advance. In addition, should the fluid fail and contribute to the equipment breaking down, this system potentially eliminates the resources required and time lost to repair/replace the underlying/broken equipment. This approach also avoids the loss of service and resources required to complete oil changes more often than actually needed.

SUMMARY OF THE INVENTION

In embodiments, an integrated system is provided for continuous monitoring of multiple properties of a fluid derived from measurements from a plurality of sensor modalities within a fluid-based closed-system environment. Suitably the system is an in-motor lubrication monitoring system and the monitoring is real-time.

In certain embodiments, the system is built into the form factor of a standard size and shaped oil drain plug found within a reciprocating engine oil drain pan, wherein said system is remotely located from a receiver by wired or wireless data telemetry. Suitably the system further comprises a remotely located receiver.

In other embodiments, the sensor modalities comprise at least two of electrical, temperature, magnetic, optical, pressure, and multi-axis accelerometer sensors, suitably at least one of the sensor modalities comprises an inductor. In embodiments, the sensor modalities comprise at least magnetic and optical sensors and in other embodiments the sensor modalities comprise at least electrical, magnetic and optical sensors.

In certain embodiments, the system is contained within an epoxy encapsulation that can support high temperature, high pressure, and high vibration environments contained within the oil drain plug mechanical design.

In certain embodiments, the system further comprises a limited lifetime power source that provides electrical energy to the electrical components of the sensor platform. In some embodiments, the system further comprises an energy scavenger/harvester that provides electrical power to a rechargeable power source for extended lifetime.

In certain embodiments, the system further comprises multiple digital signal processor modules for detection of both single and multiple related fluid characteristics. In embodiments, the systems further comprise multi-stage output signal generation selected from the group consisting of error indication, specific data signature detection signal, specific data signature signal detection strength level, and Fast Fourier Transform (FFT) data output.

In other embodiments, the sensor modality measurements are analyzed using Kalman Filtering techniques, Baysian analytic techniques, hidden-Markov Filtering techniques, fuzzy logic analysis techniques or neural network analysis techniques.

In exemplary embodiments, the sensor modality measurements comprise at least one of the following: differential temperature comparison, differential magnetic sensor comparison, differential inductive sensor comparison, differential electrical impedance comparison, differential optical absorption comparison, multi-axis accelerometer comparison, any combination and integrated comparison consisting of at least a set of two sensors, data comparison of each sensor vector versus time and temperature, data comparison of an integrated vector consisting of a set of at least two sensors combined, inductive data comparison versus time and temperature, optical data comparison versus time and temperature, optical data comparison versus temperature and pressure, temperature data comparison versus time and pressure to detect peak heat, pressure data comparison versus multi-axis accelerometer data, and other sensor combinations.

Also provided are methods of continuously monitoring an operating fluid of a machine comprising: measuring a first condition of the fluid using a first sensor modality, measuring a second condition of the fluid using a second sensor modality, filtering data from the sensors, integrating the data from the sensors, analyzing the data from the sensors, deriving a property of the fluid from the data, transmitting the derived property of the fluid condition to a receiver, and repeating the process so as to accumulate a time-series of a fluid property that tracks changes in the operating condition of the fluid. In embodiments, the methods further comprise tracking the condition of the fluid by calculating the time series expected rates of change versus observed rates of change of any single or multiple conditions. In additional embodiments, the methods further comprise calculating the expected divergence or convergence across multiple sensor time series data of anticipated and expected measured value changes versus unexpected changes.

Further embodiments, features, and advantages of the embodiments, as well as the structure and operation of the various embodiments, are described in detail below with reference to accompanying drawings.

DETAILED DESCRIPTION OF THE INVENTION

Figure 1:
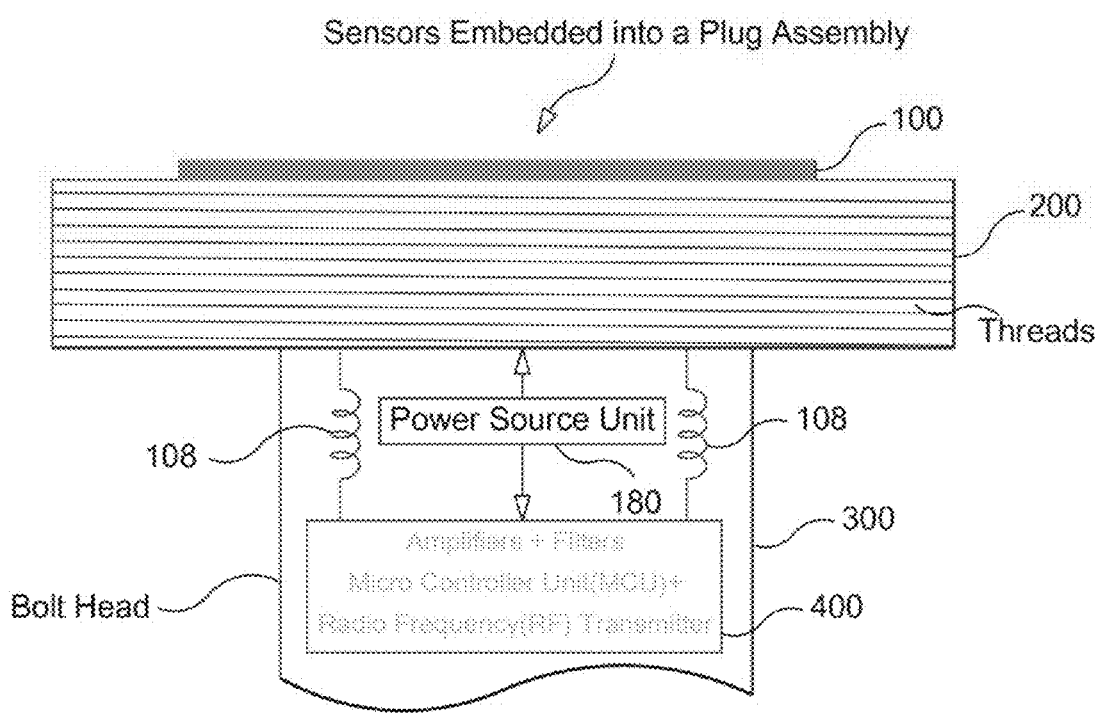
FIG. 1 is a representation of an exemplary real-time multi-modal fluid sensing system described in this application.
Figure 2:
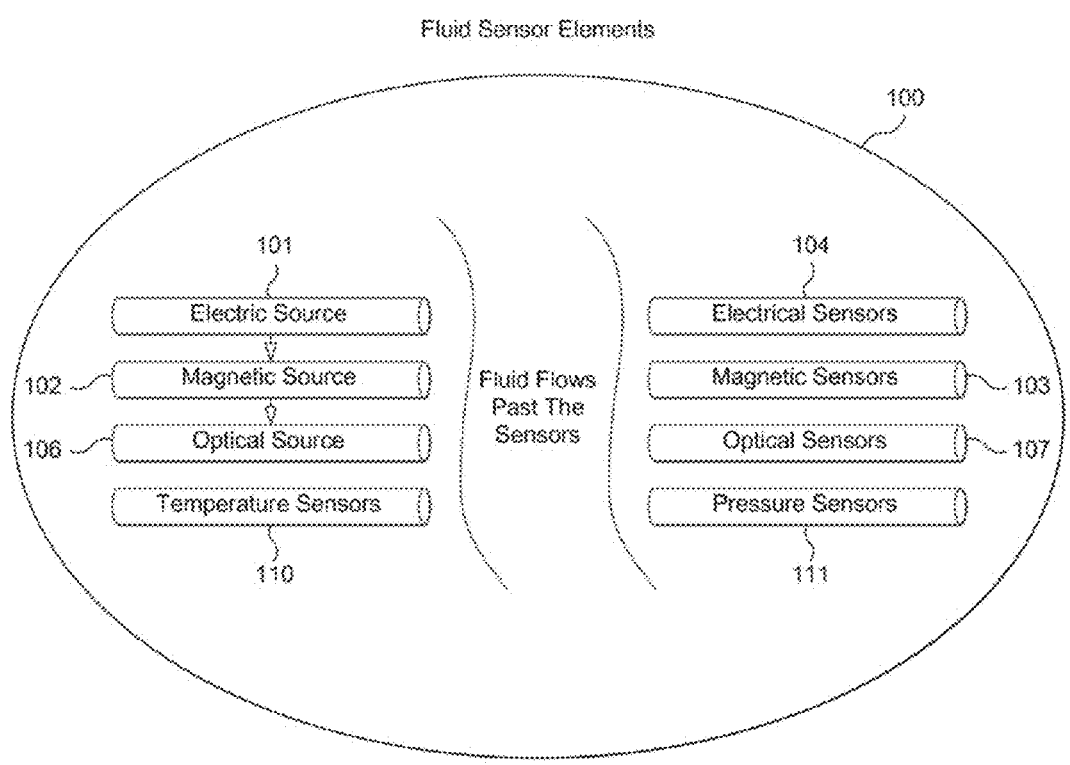
FIG. 2 is a representation of an exemplary major in-engine sensor source and receiving elements making up the multi-modal fluid sensor solution.
Figure 3:
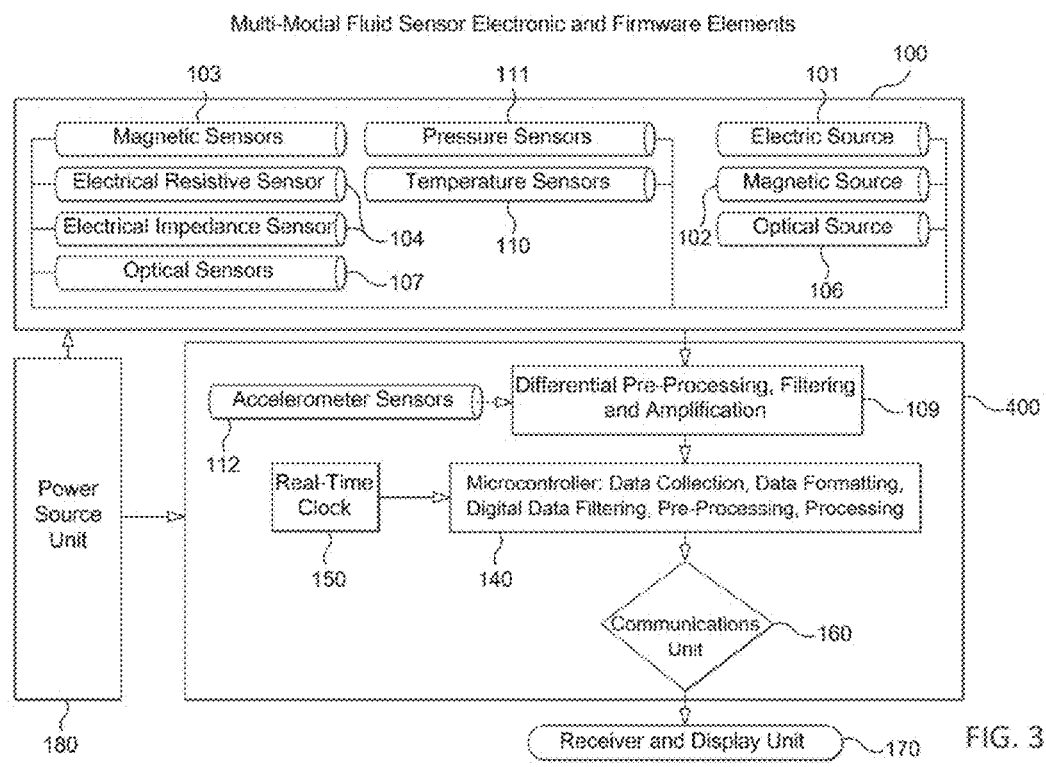
FIG. 3 is a block representation of an exemplary major electronic and firmware elements of the system presented within this application.
Figure 4:
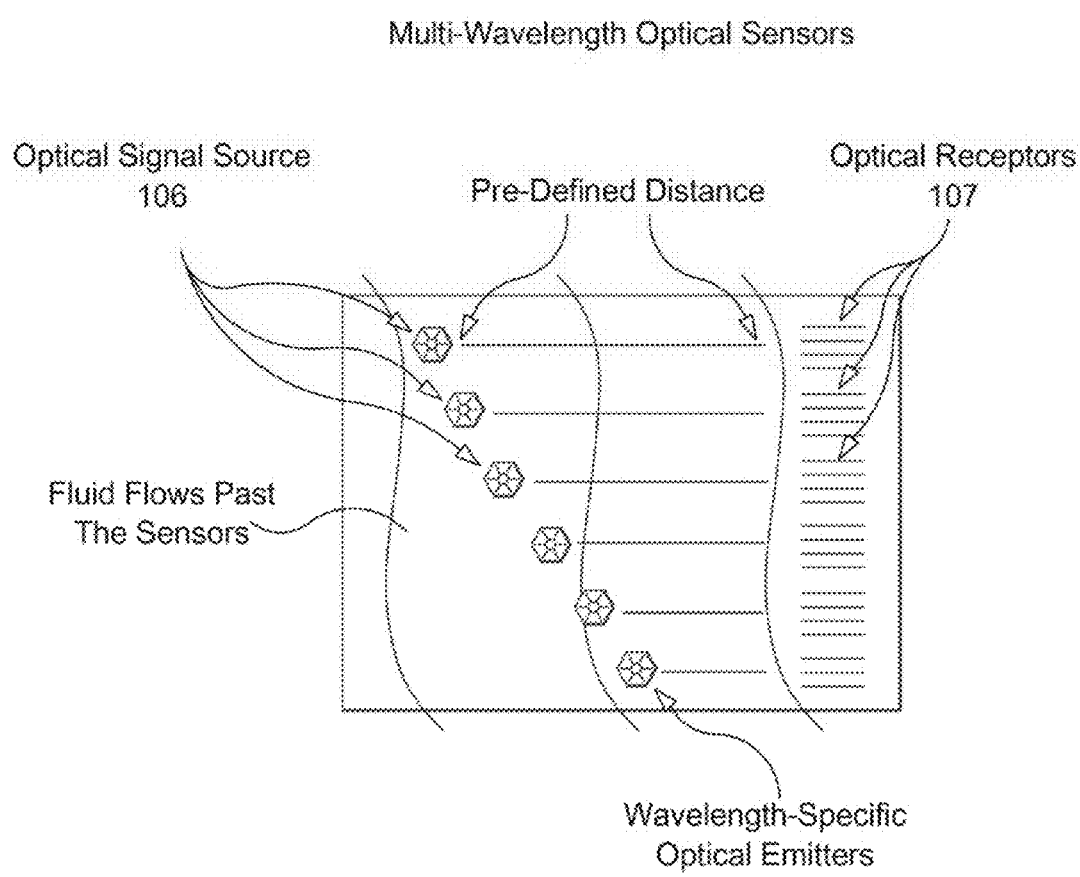
FIG. 4 is an inset diagram of exemplary optical sensors.
Figure 5:
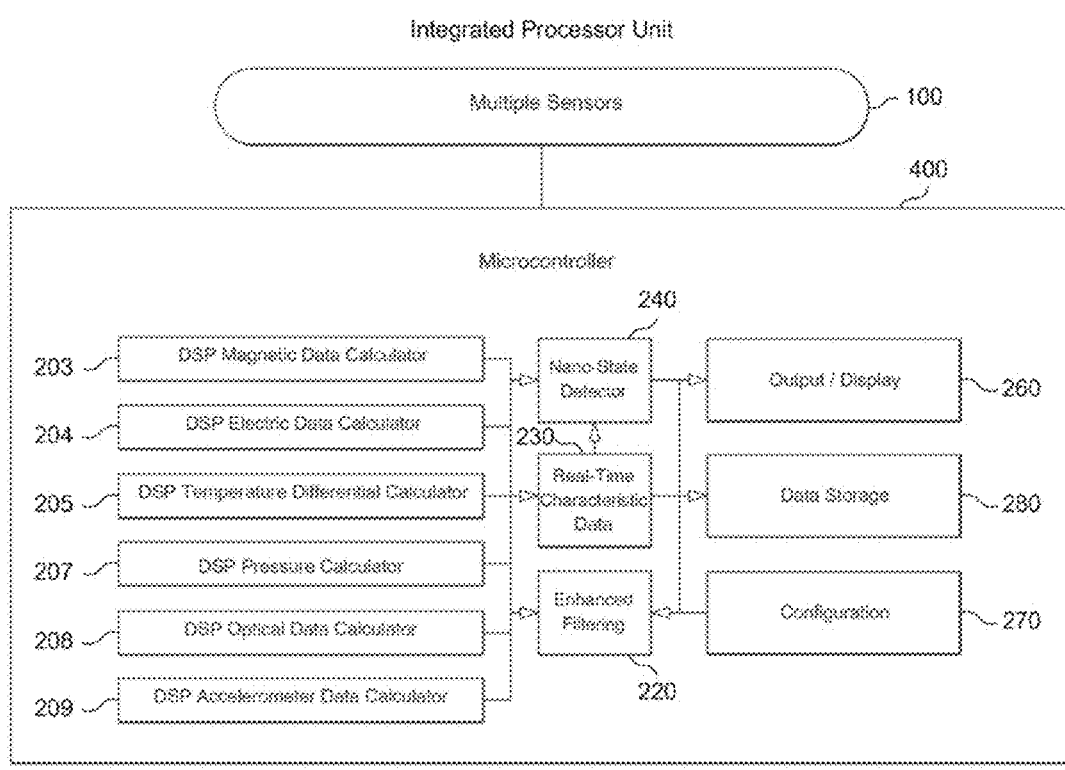
FIG. 5 is a block diagram of exemplary processing electrical and/or firmware elements comprising the Digital Signal Processing modules incorporated within the processing portion of the system presented within this application for integrated multi-modal sensor calculations.

It should be appreciated that the particular implementations shown and described herein are examples and are not intended to otherwise limit the scope of the application in any way.

The published patents, patent applications, websites, company names, and scientific literature referred to herein are hereby incorporated by reference in their entirety to the same extent as if each was specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter.

As used in this specification, the singular forms "a," "an" and "the" specifically also encompass the plural forms of the terms to which they refer, unless the content clearly dictates otherwise. The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%. It should be understood that use of the term "about" also includes the specifically recited amount.

Technical and scientific terms used herein have the meaning commonly understood by one of skill in the art to which the present application pertains, unless otherwise defined. Reference is made herein to various methodologies and materials known to those of skill in the art.

To provide a more accurate understanding of a fluid, conducting multi-modal tests simultaneously can help to give insight into the true operating status and condition of the lubricating fluid. In embodiments, an integrated system is provided for continuous monitoring of multiple properties of a fluid derived from measurements from a plurality of sensor modalities within a fluid-based closed-system environment. Suitable embodiments utilize a combination of advanced Micro-Electro-Mechanical Systems (MEMS) and semiconductor techniques to place the laboratory tests directly into the fluid to continuously and concurrently measure multiple aspects of the fluid and report these parameters individually to a programmable computer to provide parallel and integrated real-time analysis of the fluid condition. As used herein the term "sensor modalities" include measurement of the magnetic, electrical and optical properties of a fluid as well as measuring the temperature and pressure of the fluid and monitoring the orientation of the fluid and surrounding containment vessel in space by measurement of multi-axis acceleration. These collectively comprise examples of "multi-modal" analysis or tests throughout the present invention. These measurements can be done both individually and combined—to provide an integrated insight into the condition and status of the fluid. As single-dimension tests may "obscure" any single result caused by the interplay between two different contaminants in the fluid (e.g. the combination of both electrical resistance increasing and electrical resistance decreasing foreign matter in the system), the application of simultaneous multi-modal sensing using a plurality (i.e., two or more) sensing modalities improves the fidelity and accuracy of the measurements.

In multi-modal sensing, measurements are combined to determine the state (and state changes) for the fluid using software/firmware programming to compare sensor inputs against reference datum and to detect changing fluid conditions across various measurement dimensions, including time. It is important to set thresholds for detection of foreign contaminants in the oil. For example, a sufficient quantity of water over time can cause corrosion of critical elements normally protected by the lubricating fluid. Based on these thresholds, certain alerts and notices can be provided, either transmitted through an output interface or polled by a wireless interface, optionally using a portable hand-held device, such as a smart phone. To validate the ongoing assessment of the fluid condition, a secondary check can be done to verify the measurements through periodic laboratory sampling. External validation can be part of the conforming calibration process during initial testing of the multi-modal sensors. External validation can also qualify additional lubricating fluids and operating environments. Once the baseline is understood, the thresholds across all the integrated measurements can be programmed into the semiconductor to provide the alerting functionality over and beyond the integrated measurement data outputs.

In additional embodiments, the systems and methods described herein detect use of the wrong fluid or unsuitable lubricating fluid that may be mistakenly introduced into the lubrication system. Operating machinery with the wrong lubricating fluid can cause irreparable harm if not immediately remediated. The multi-modal sensor 'expects' lubricating fluid to be conforming, raising an alert when non-conforming fluid is introduced and subsequently detected.

Specific individual sensors can be combined into a framework that provides a much more complete understanding of the state of the system, both for immediate measurement as well as longitudinal monitoring. Such sensor frameworks greatly improve real-time monitoring of system conditions and greatly improve the ability of the system to automatically recognize and respond to a variety of operational events.

In particular, frameworks incorporating magnetic sensors facilitate the timely recognition of ferrous metal contaminants. For example, paramagnetic resonance can characterize the nature of the ferrous particles, and potentially their size.

Integrating optical transmissometers, opacity measurements or spectral measurements into the framework provides an indication of particular contaminants, for example, soot, water, or antifreeze solution. Further the invention can be improved through the incorporation of multi-modal sensing analysis to include for example pressure and temperature that may change the optical properties of the fluid. These correcting factors can be applied to improve the accuracy of the measurements.

Integrating electrical measurements into the framework provides a more complete picture of the fluid condition. These measurements can also detect and can provide independent ways to distinguish between alternative fluid status and condition diagnoses. This state change is detectable by a set of at least one of the sensor modalities.

A control system integrates disparate sensors, utilizing patterns of sensor conditions to "recognize" or "diagnose" sets of conditions worthy of further attention. Established mathematical algorithms for such analysis include and are not limited to Kalman filtering (and enhanced Kalman filtering), hidden-Markov models, Bayesian analysis, artificial neural networks or fuzzy logic. These control systems can be implemented readily in software, firmware or hardware, or a combination thereof (See: "Solutions for MEMS Sensor Fusion," Esfandyari, J, De Nuccio, R, Xu, G., Solid State Technology, July 2011, p. 18-21; the disclosure of which is incorporated by reference herein in its entirety)

In further embodiments, additional understanding of the fluid properties under different machinery operating conditions can be gained, for example, including "at rest" when the system is not operating, or at "peak heat," which may actually occur after the system shutdown. Temperatures may increase after shutdown when no cooling fluid is circulating. Fluid properties will change as the fluid heats and cools. Measuring these changes across the short heating or cooling interval can yield valuable additional indications and insights into the properties of the lubricating fluid. For example, optical absorption may vary as the fluid heats. In addition, tracking the change in electrical properties with temperature can provide further information as to the condition of the fluid. Deviations may cause the control system to request measurements not only when the machinery is operating but also upon startup or shutdown, for example.

The present application overcomes a number of limitations of traditional diagnostics. First, the traditional time delay from fluid sampling to testing may place critical equipment at risk of damage. Sometimes the lubricating fluid is sampled at the time it is being exchanged. While potentially useful for providing insight into the wear of internal parts, machinery may be operated in a potentially unsafe condition until the results are returned from the laboratory. Second, the lubricating fluid may be exposed to extreme temperatures during operating transients, which can be often in excess of 150 degrees C., potentially causing some breakdown of additives in the lubricating fluid. Such problems are not usually detected, as the equipment often is "turned off" during these conditions. Although there is no new heat being generated, residual heat is transferred into the lubricating fluid and can potentially impact its performance. Such temperature extremes often require special engineering effort to design integrated in-situ sensing systems to support reliable operation (e.g. from −50 C to +150 C). Further, sensors and other electrically active elements need to support this environment. Equally important is the support of various pressures that the lubricating fluid may experience during normal and high-load operations. An in-situ sensor framework must be designed to withstand the peak temperatures and pressures experienced within the lubrication system over time.

Several variables provide insight into lubrication fluid properties. Some variables can be measured directly while others can be derived. To achieve a basic understanding of fluid condition, several measurements (sensor modalities) of the lubricant may be helpful, including, for example, temperature, absolute pressure, electrical impedance or resistance, pH, optical transmission or absorption, and magnetic measurements. Measurements are either direct (e.g. temperature via a temperature sensor) or derived—such as degree of carbon buildup via combined measurement of electrical and optical changes. Standard techniques are available and used today such as thermocouples and pressure sensors to acquire some of these data points. Derived measurements (e.g. viscosity conformance within operating range) can be calculated from direct measurements, and can be extrapolated over ranges of temperature and pressure. Additional detection methods include the use of one or more inductive coils and magnetic sensors to enhance detection of moving metallic particles. An optical transmissometer, comprised of an optical light source and optical detector, for example, measures the changes in absorption of optical light at various wavelengths to characterize carbon soot buildup and other potential contaminants and materials in the lubricating fluid. All such measurements should be temperature and pressure compensated (or normalized) to provide an accurate indication of the underlying health of the lubricating fluid. Further, pressure measurements can be qualified for changes in the system orientation. Computation of orientation from multi-axis accelerometers is used to determine when a pressure reading may be invalid due to the system being oriented beyond a predetermined standard, or alternatively the pressure reading is compensated for a system orientation within predetermined limits of such a standard.

Viscosity analysis derives a frictional index from multiple sensor readings to determine the net fluidic friction of the lubricant. This invention presents a simple method of deriving viscosity by measuring, for example, two magnetic sensors within the fluidic lubricant in a selected site to measure fluid flow. These magnetic sensors, such as no-latency Hall sensors, are substantially similar and located in close proximity to one another within the lubricant flow. A small turbulence inducer enables measurement near the sensors of slight differences in flow based on induced flow perturbation. This measure can be further integrated with optical absorption measurements using the optical transmissometer. This integrated measure, coupled with temperature or qualified pressure readings, provides a framework for calculating the frictional index. The Hall-based sensors are designed to be as similar as possible. Temporal and spatial variations not caused by the turbulence inducer are subtracted using the two nearly identical sensors. Further, the shape of the turbulence inducer is designed to create subtle changes related to the fluidic velocity, analogous to aeronautical applications in which fluid molecules travel at slightly different speeds above and below an airfoil. Viscosity can be derived from these slight difference measurements along with the local temperature and pressure, using documented lubricant viscosity reference data, providing an indication of real-time lubricant conditions.

Sensors are suitably designed to withstand high temperatures of the engine lubricant. High-temperature thermocouples measure temperature, thick-film resistors enable pressure sensing, and high-temperature magnetic sensors. The optical measuring methods are based on proven high-temperature designs. The optical spectrum suitably ranges from UV to mid-IR in which the lubricating fluid is not emitting energy at high temperature, depending on the fluid and the environment and potential contaminants. The transmissometer range is measured in millimeters and the distance between the emitting element and the receiving element is precisely controlled using known MEMS manufacturing techniques. This distance between the optical emitting and receiving elements must be very accurate. All of these elements have been implemented and operate individually within these extreme temperature and pressure environment in such a manner as to relay useful data. The design is not limited to these methods. At present, these methods are proven effective and provide a simple solution.

In embodiments, the systems and methods described throughout provide real-time monitoring of fluids such as those associated with high-temperature environments present within or associated with internal combustion engines (i.e., monitoring the fluid during engine activity without the delay of removing a sample). Suitably, the systems and methods monitor oil-based fluid lubricants normally used with internal combustion engines, as well as other fluids such as transmission fluids or glycol-based coolants such as antifreeze, and other fluids in manufacturing environments and critical life-saving medical equipment used in the healthcare industry. The systems and methods suitably provide real-time monitoring using multiple sensor modalities to determine the degradation of the monitored fluid under various operating conditions. Another aspect is the ability of the invention to detect the presence of known harmful particulates, such as metal, within the lubricant. Another aspect addressed is monitoring fluid with a sensor module that is continually submersed within the lubrication fluid. Another aspect addressed is the parallel and integrated real-time analysis of the fluid condition. This invention also addresses high temperatures and other conditions experienced in the operating environment of such machinery.

In exemplary embodiments a real time multi-modal fluid sensing system is in a self-contained embodiment of a single unit comprising an active sensing environment (100) intended to be submerged in the fluid to be monitored. The sensors are attached to an assembly that can be placed into the fluid with the electronic and active sensors embedded into a oil drain plug (300) that is held in place via a threaded bolt (200). The bolt head accommodates the non-sensor elements of the self-contained system, called the command, control and communications module, C3 module (400) to include the microcontroller, filters and other elements. Also suitably contained within the assembly are inductor coils (108) and other methods of signal source to include power to operate the system, such as a power source (180). The bolt assembly is a self-contained platform that can be installed and removed by a technician. Such an environment is typical of an oil drain plug on an automobile or a similar "low point" in a lubricating return system that may also serve as a reservoir for the fluid. The fluid environment may be subject to changes in temperature and pressure through normal and abnormal operations. As such the sensors are designed to operate within the temperature and pressure specifications—as well as customary tolerances beyond the normal operating environment to be able to detect abnormal conditions.

Within the sensing environment the system programmatically generates its own local and low energy reference signal sources across multiple sensor modalities including magnetic, optical and electrical, and continuously detects values therein as well as passively receives continuous pressure and temperature measurements. The active elements of the sensor platform (100) are intended to be submerged in the fluid under measurement. In the case that the sensor is not submersed, either completely or partially into the fluid, this can be detected and confirmed through multiple sensor confirmation across the optical (106) transmission to optical reception (107) as well as electrical source (101) to reception (104) of expected value tolerances. In this way the condition of lack of fluid can be detected by multiple approaches, as well as verify that both the electrical and optical sensors are correctly and collaboratively cross-checked.

Magnetic sensing is achieved through generating a signal of a pre-defined and programmable characteristic (102) that has a known fixed reference distance within close proximity to the magnetic sensors (103) that is received and processed by a data acquisition control unit (109) that performs signal amplification, A/D conversion and data filtering. The sensing can be accomplished by one or more sensors (103) of a type such that provide a response rate commensurate with the signal, that can be the same type or different and provide both direct and differential measurements of the fluid condition. The data acquisition control unit (109) performs the steps to filter and analyze the signals, including amplification, noise reduction filtering which is then communicated to the microcontroller (140).

Figure 6:
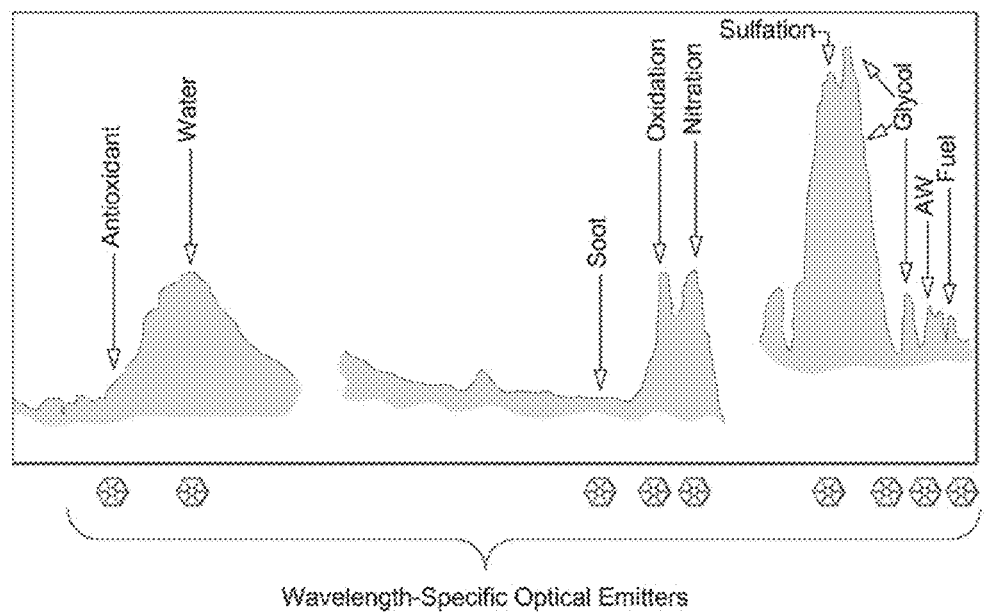
FIG. 6 is a representative framework of discrete wavelengths for the various optical properties detection.

One or more optical sensors (107) can be coupled to one or more optical source(s) (106) which can consist of one or more specific optical wavelength emitters such as narrow frequency tuned light emitting diodes (LEDs) and optical receivers such as photoreceptors. Today's optical emitters can be configured to emit light in narrow frequency bands. Such wavelengths are dependent upon the specific types of fluid and contaminants that may accumulate within the fluid. FIG. 6 shows a representative map over the near infrared region of such. The optical sensing can determine a number of characteristics, including but not limited to the presence of fluid, when the LED is emitting. Further the LEDs can be placed at different known and fixed distances from accompanying photoreceptors to provide a distance based profile of the level of absorption across different frequencies. The embodiment can be accomplished by a single LED emitter to photoreceptors at known distances as well as multiple LEDs spaced at known distances from the photoreceptor pulsed in a known sequence. The controlling logic is managed through software/firmware in the microcontroller (140) and in the data acquisition control unit (109). Optical sensing can detect the difference in both the specific wavelength absorption and time series changes in optical characteristics. The optical sensing developed operates in both an active and passive mode. In the active mode the optical source pulses light of known strength and wavelengths through the fluid to measure the degree and level of absorption of the light from its source. This small scale transmissometer is configured to detect the specific contaminants and/or changes such as a breakdown in the fluid properties across specific wavelengths, such as shown in FIG. 6.

Sensing changes in the electrical properties is accomplished by an electric source (101) placed at known reference distance from an electric capacitive measuring such as the constant of dielectric of the fluid. The strength and frequency of signal and measurement is based on the programmable microcontroller firmware and is based and dependent on the underlying characteristics of the fluid to be continuously monitored which lies between the source and measurement sensing. The electric resistance and capacitance can be measured across the gap via the data acquisition control unit (109). Different fluids will have different properties, and thus the ability to programmatically configure and control both the source field and sensor receiving properties is an important aspect of this invention. Pressure sensing (111) and temperature sensing (110) are also connected to the data acquisition control unit (109). These sensors can also detect normal and abnormal conditions in heat and pressure levels and provide insight to the operating status of the environment. Fluid condition changes—such as at rest (when the system is not operating) through the peak operating environment —can be evaluated by the programmable microcontroller unit (140). Such applications can be developed in software/firmware to include developing an understanding of both "at rest" and "in operating" conditions. Further, the profile at specific pressures and temperatures can be useful for both determining calculations (offsets due to temperature/pressure—such as if magnetic sensors are based on using the Hall Effect (103)) as well as optical property changes due to temperature and pressure profiles.

Tracking changes in the orientation of the oil drain plug (300) of FIG. 1 in three-dimensional space is accomplished by multi-axis accelerometer sensors (112). Note that in alternative embodiments, accelerometer 112 may be disposed in the C3 module (400), MEMS sensor platform (100), receiver (170), or other external location. The accelerometer sensor (112) may be disposed in the MEMS device (100), in the non-sensor elements of the self-contained system, called the command, control and communications module, C3 module (400), or near another processor unit. The acceleration of each axis of interest is measured by the data acquisition control unit (109) and used to compute the orientation of the oil drain plug (300), and therefore the orientation of the engine and of the vehicle in space. The orientation computation can be used by the data acquisition control unit (109) to qualify the measurements from the pressure sensors (111) and reject certain pressure readings or make adjustment to certain pressure readings to compensate the pressure output, according to predetermined standards of orientation.

A real time clock (150) provides an accurate time basis to trigger monitoring events by the microcontroller module (140) and associate acquired data with a time basis for longitudinal analysis. The real time clock provides both time and date information that can be associated with each of the recorded multi-modal sensor measurements.

The programmable microcontroller (140) also provides both pre and post processing of information including the use of filtering and other algorithms to provide data correction. The results are communicated via a communications module (160) either via a wired or wireless connection to a receiver (170). Note that receiver 170 may optionally comprise a display, a processing unit, or both, receiving data from the integrated system. Both the receiver (170) and the microcontroller may possess internal storage (280) to record and evaluate time-series data.

Within the microcontroller (140) sensor data is accumulated and subject to additional filtering and integration across the multiple sensors. The raw data is subject to processing by a set of at least one digital signal processor (DSP) for each of the individual sensor modalities such as temperature, pressure, optical absorption, electrical impedance and magnetic signature (203, 204, 205, 206, 207 and 208). A parallel output of the results—both pre and post data correction filtering (220) provides both a raw data output (260) that can be communicated via a communications module (160).

A configuration module (270) can dynamically set filtering and processing parameters to the enhanced filtering (220) to include baseline and error conditions as well as other parameters including configuring storage, event monitoring, triggers, etc. The configuration module is connected via the communications module (160) to an external device.

Further, during operation that can be either continuous or polled at intervals as directed by the microprocessor and associated programming software, and further enhanced by the inclusion of a real time clock to provide an accurate time basis (150). Such measurement "cross checking" provides for both inherent value confirmation, improves that data correction (by example Kalman filtering and other algorithmic techniques) and overall sensor system integrity. For many high value systems when a "fault" is detected, often the failure is not in the environment, but the sensor. This invention provides for the cross-correlation and verification of the inherent sensor platform by continuously validating across a number of the measurement criteria such that expected and anticipated sensor output/values can continuously validate the sensor system performance. In this way the isolation of the error condition (e.g. the sensor failure) is in itself a valuable operator insight—to identify and replace a faulty sensor as a known failed device.

A power source (180), comprising electrical storage (182) and an optional energy harvester, provides electrical power to the C3 module (400) and sensor platform (100). In one embodiment, the electrical storage comprises a battery that provides power to the system until it is discharged. In another embodiment, the electrical storage comprises a rechargeable battery connected to one or more energy harvesters, which extend the lifetime of the electrical storage beyond a single charge. In another embodiment, the power storage comprises an electrical double layer capacitor, optionally coupled to an energy harvester that extends the lifetime of the electrical storage beyond a single charge.

In one embodiment, the energy harvester comprises a vibration energy harvester (183) that converts kinetic energy from the environment into an electrical current. In another embodiment, the energy harvester comprises an acoustic energy harvester (184) that converts audible or vibrational energy into an electrical current. In another embodiment the energy harvester comprises a thermal energy harvester (185) that converts differential temperatures into an electrical current. In another embodiment the energy harvester comprises an electromagnetic energy harvester (186), where an antenna (188) collects background electromagnetic radiation, such as RF transmissions, for conversion into an electrical current.

The C3 module (400) communicates with the Receiver (170) using either wired or wireless protocols, or both. Suitable protocols exist in automotive systems today, such as Controller Area Network bus (CAN) and Local Interconnect Network bus (LIN) for wired communications, and Tire Pressure Monitoring System (TPMS) and Remote Keyless System (RKS) for wireless communications. The Receiver (170) in some embodiments could comprise a processing unit. It could also comprise a display for depiction of the monitoring status.

The mechanical design for sensing changes in fluid parameters in-situ incorporates unique features to minimize costs and provide an environmentally sound design for long life. The concept is to include a pressure sensor device built into the oil drain plug that allows for simple installation for upgrades and replacement on scheduled maintenance schedules. The sensor is mounted with an epoxy polymer resin that has an excellent operating temperature range, adherence properties, and resistance to salts and petroleum by products. This is a key to prevent issues with differential thermal expansion, delamination, and chemical breakdown. The bolt has a standard thread size based on the end users specification. A hole is drilled through the middle of the bolt to allow for installation of the integrated system and to provide a path for the oil to reside over the sensor platform (100). The outside of the pressure sensor is open to the atmosphere via an integrated atmospheric pressure pipe (314). The head of the bolt is machined down to fit the sensor into the bolt by creating a cavity.

Figure 7:
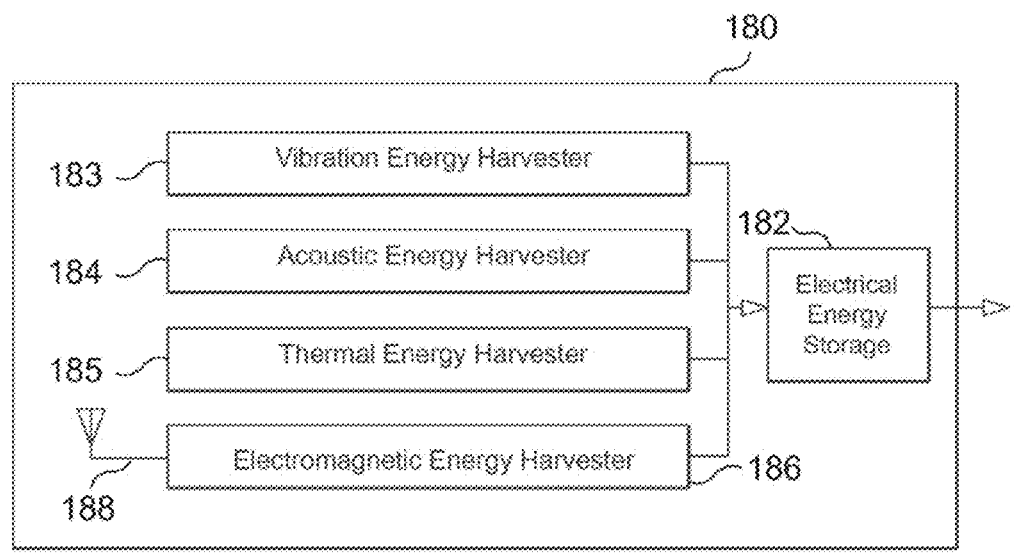
FIG. 7 is a block representation of an exemplary power unit for the system presented in this application.

FIG. 7 depicts a power source comprising energy storage (182) and/or an energy harvester (183-186) for adding to the energy storage (182). Such energy harvesters could collect vibrational energy (183), especially from the oil pan of an operating engine, or acoustic energy (184). Many embodiments also comprise a thermal gradient between fluid pan and the environment, in which harvester (185) could comprise a TEC (Thermo-Electric Converter) for the conversion of thermal to electric energy, as is known to those of skill in the art. Alternatively, Electromagnetic Harvester (186) could collect energy from any one of electric field, magnetic field, inductive, wired or wireless electromagnetic energy, optionally using antenna (188).

Figure 8:
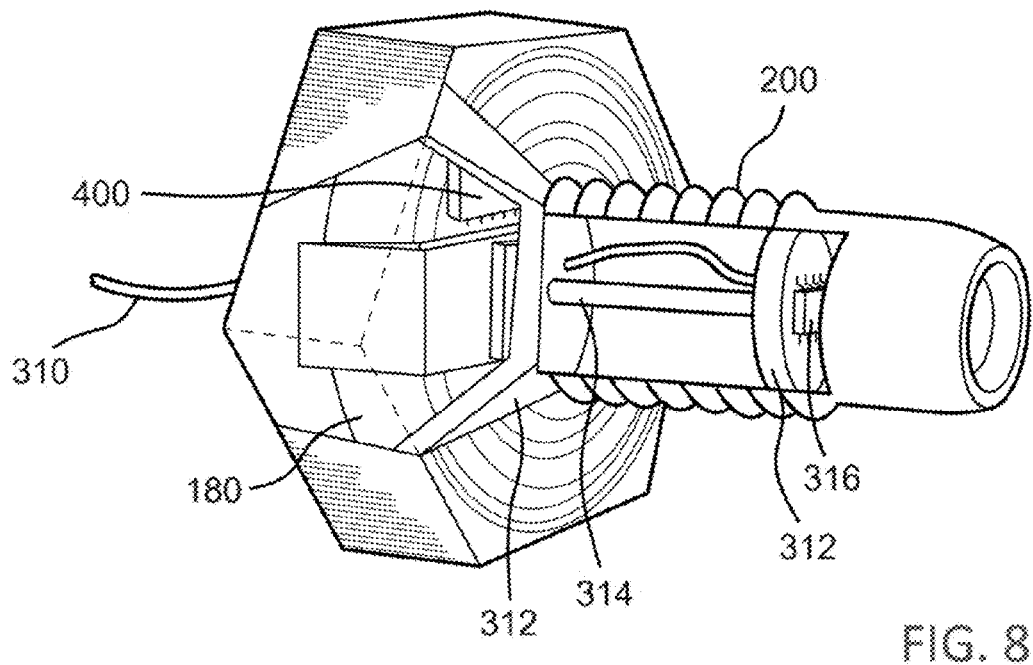
FIG. 8 is a representation of an exemplary real-time multi-modal fluid sensing system presented in this application in the exemplary form factor of a standard oil drain plug.

FIG. 8 depicts an overall cutaway view of the oil drain plug multi-modal sensor system, showing one particularly favorable embodiment of the present invention, including C3 module (400), integrated MEMS sensor platform (316, equivalent to sensor platform 100), and battery (180). RF antenna (310) provides communications and in some embodiments performs the energy havesting of antenna (188). Printed circuit boards (312) shown in cutaway view provide one or more substrates and electrical coupling for C3 module (400) and MEMS sensor platform (316 or 100). Ambient pressure pipe (314) conveys the ambient pressure to a differential pressure sensor disposed in this embodiment on sensor platform (316). Note that other embodiments could use an absolute pressure sensor in place of this differential sensor, with or without an additional ambient pressure sensor to enable an electrical compensation as opposed to mechanical pressure compensation. Temperature compensation is also known to those of skill in the art for these pressure sensors to improve accuracy and repeatability. Bolt threads (200) provide a conformal drop-in replacement for a traditional oil drain pan bolt in some preferred embodiments.

In one embodiment, this sensor system measures the pressure near the bottom of the fluid reservoir, and optionally compares this pressure to ambient pressure. Optionally temperature compensation may be included for this measurement. This approach can measure the mass of fluid in a column above the sensor corresponding to the static pressure in a gravitational (or accelerational) field. For a given temperature, this static pressure approximates the level of the fluid at a particular temperature and orientation of the fluid-containing vessel.

The foregoing description, for purpose of explanation, has been described with reference to specific embodiments. The illustrative discussions above, however, are not intended to be exhaustive or to limit the invention to the precise forms disclosed. Many modifications and variations are possible in view of the above teachings. The embodiments were chosen and described in order to explain the principles of the invention and its practical applications, to thereby enable others skilled in the art to best utilize the invention and various embodiments with various modifications as are suited to the particular use contemplated.

What is claimed is:

1. An integrated system for continuous monitoring of multiple properties of a fluid comprising:
    a bolt comprising one or more sensors and one or more non-sensor elements embedded within the bolt for continuous monitoring of multiple properties of a fluid derived from measurements from a plurality of sensors within a fluid-based closed-system environment, wherein the one or more non-sensor elements comprise a radio frequency transmitter, and an aperture at an end of the bolt to allow the one or more sensors to contact said fluid.

2. The integrated system of claim 1, wherein said system is an in-motor lubrication monitoring system.

3. The integrated system of claim 1, wherein said monitoring is real-time.

4. The integrated system of claim 1, additionally comprising a remotely located receiver unit.

5. The integrated system of claim 1, built into a standard size and shaped oil pan plug bolt found within a reciprocating engine oil drain pan, wherein said system is remotely located from said receiver unit, conveying monitoring information from said system to said receiver unit by data telemetry.

6. The integrated system of claim 1, wherein the sensors comprise at least two of electrical, temperature, magnetic, optical, acceleration, and pressure sensors.

7. The integrated system of claim 1, wherein at least one of the sensors comprises an inductor.

8. The integrated system of claim 1, wherein the sensors comprise at least magnetic and optical sensors.

9. The integrated system of claim 1, wherein the sensors comprise at least electrical, magnetic and optical sensors.

10. The integrated system of claim 1, contained within an epoxy encapsulation that can support high temperature, high pressure, and high vibration environments.

11. The integrated system of claim 1, further comprising multiple digital signal processor modules for detection of both single and multiple related fluid characteristics.

12. The integrated system of claim 1, further comprising multi-stage output signal generation selected from the group consisting of error indication, specific data signature detection signal, specific data signature signal detection strength level, and Fast Fourier Transform (FFT) data output.

13. The integrated system of claim 1, wherein the sensors measurements are analyzed using Kalman Filtering techniques.

14. The integrated system of claim 1, wherein the sensors measurements are analyzed using Baysian analytic techniques.

15. The integrated system of claim 1, wherein the sensors measurements are analyzed using hidden-Markov Filtering techniques.

16. The integrated system of claim 1, wherein the sensors measurements are analyzed using fuzzy logic analysis techniques.

17. The integrated system of claim 1, wherein the sensors measurements are analyzed using neural network analysis techniques.

18. The integrated system of claim 1, wherein the sensors measurements comprise at least one of the following:
    a Differential temperature comparison;
    b Differential magnetic sensor comparison;
    c Differential inductive sensor comparison;
    d Differential electrical impedance comparison;
    e Differential optical absorption comparison;
    f Any combination and integrated comparison consisting of at least a set of two sensors;
    g Data comparison of each sensor vector versus time and temperature;
    h Data comparison of an integrated vector consisting of a set of at least two sensors combined;
    i Inductive data comparison versus time and temperature;
    j Optical data comparison versus time and temperature;
    k Optical data comparison versus temperature and pressure;
    Temperature data comparison versus time and pressure to detect peak heat; and
    m Other sensor combinations.

19. An in-motor lubrication monitoring system for continuous real-time monitoring of multiple properties of a fluid derived from measurements from a plurality of sensor modalities within a fluid-based closed-system environment comprising:
- (i) a bolt comprising one or more sensors imbedded within the bolt for continuous monitoring of multiple properties of a fluid, wherein the bolt comprises an aperture at an end of the bolt to allow the one or more sensors to contact said fluid; and
- (ii) a multi-stage output signal generation selected from the group consisting of error indication, specific data signature detection signal, specific data signature signal detection strength level, and Fast Fourier Transform (FFT) data output.

20. The integrated system of claim 19, wherein the in-motor lubrication monitoring system comprises an oil plug bolt found within a reciprocating engine oil drain pan.

21. The integrated system of claim 19, wherein said system is remotely located from a receiver unit by wired or wireless data telemetry.

22. The integrated system of claim 19, additionally comprising a remotely located receiver unit.

23. The integrated system of claim 6, wherein the sensors modality of pressure is qualified by the sensors of acceleration.

24. The integrated system of claim 1, wherein the system is powered by an electrical power source comprised of at least one of the following:
- a A non-rechargeable electrical battery;
- b A rechargeable electrical battery;
- c An electrical double-layer capacitor;
- d An energy harvester that converts vibrational energy to an electrical current;
- e An energy harvester that converts acoustic energy to an electrical current;
- f An energy harvester that converts a temperature difference to an electrical current;
- g An energy harvester that converts electromagnetic energy to an electrical current; and
- h Other forms of energy harvesting.

25. The integrated system of claim 1, the system also comprising a microcontroller unit that processes the sensors' readings.

26. The integrated system of claim 1, further comprising a communications unit capable of at least one of the following couplings:
- a Wireless coupling from said system to the receiver unit;
- b Wireless coupling from the receiver unit to said system;
- c Wireline coupling from said system to the receiver unit; and
- d Wireline coupling from the receiver unit to said system.

27. The communications unit of claim 24, wherein the communications unit comprises at least one of the following:
- a In-vehicle wireless communications;
- b Tire Pressure Monitoring System (TPMS);
- c Remote Keyless System (RKS);
- d In-vehicle wireline communications;
- e CAN bus; and
- f LIN.

28. The integrated system of claim 1 disposed within an oil drain pan bolt of an engine.

29. The integrated system of claim 1, wherein the monitoring of multiple properties detects nonconforming fluids introduced into the fluid-based closed-system environment by measuring non-conforming properties of the fluid being monitored.

30. The system of claim 1 for monitoring multiple properties, wherein the level of the fluid in the closed system comprises one of the properties, and wherein one of the sensors comprises pressure sensing.

31. The integrated system of claim 1, wherein a method of signal source from a battery includes power to operate the system.

32. The integrated system of claim 31, wherein the battery is charged by an electrical current provided by at least one of the following methods of signal source to include power to operate the system:
- a. a source that converts vibration energy to an electrical current;
- b. a source that converts heat energy to an electrical current; and
- c. a source that converts electromagnetic energy to an electrical current.

33. The integrated system of claim 1, wherein a signal source from a capacitor includes power to operate the system, and wherein the capacitor is charged by an electrical current provided by at least one of the following methods of signal source to include power to operate the system:
- a. a source that converts vibration energy to an electrical current;
- b. a source that converts heat energy to an electrical current; and
- c. a source that converts electromagnetic energy to an electrical current.

34. The integrated system of claim 33, wherein the capacitor is an electric double layer capacitor.

* * * * *